(12) United States Patent
Matsuda et al.

(10) Patent No.: US 8,797,399 B2
(45) Date of Patent: Aug. 5, 2014

(54) APPEARANCE INSPECTION APPARATUS

(75) Inventors: Shinya Matsuda, Suita (JP); Hiroshi Aoki, Suita (JP); Toshiaki Onoe, Suita (JP)

(73) Assignee: Daiichi Jitsugyo Viswill Co., Ltd., Osaka (JP)

( * ) Notice: Subject to any disclaimer, the term of this patent is extended or adjusted under 35 U.S.C. 154(b) by 406 days.

(21) Appl. No.: 13/108,676

(22) Filed: May 16, 2011

(65) Prior Publication Data

US 2011/0285841 A1     Nov. 24, 2011

(30) Foreign Application Priority Data

May 20, 2010   (JP) ................................. 2010-116044

(51) Int. Cl.
*H04N 7/18*     (2006.01)
(52) U.S. Cl.
USPC ..................................... 348/92; 348/E07.085
(58) Field of Classification Search
USPC ............................................ 348/92, E07.085
See application file for complete search history.

(56) References Cited

U.S. PATENT DOCUMENTS

| | | | | |
|---|---|---|---|---|
| 5,473,426 | A  * | 12/1995 | Hayano et al. | 356/237.2 |
| 6,657,771 | B2 * | 12/2003 | Okayama | 359/290 |
| 6,980,291 | B2 * | 12/2005 | Saito | 356/237.2 |
| 7,474,392 | B2 * | 1/2009 | Van Soest | 356/52 |
| 7,553,110 | B2 * | 6/2009 | Minami et al. | 406/75 |
| 2002/0024677 | A1 | 2/2002 | Metcalfe et al. | |
| 2003/0189703 | A1 * | 10/2003 | Yonezawa et al. | 356/237.2 |
| 2004/0114153 | A1 * | 6/2004 | Andersen et al. | 356/606 |
| 2004/0119971 | A1 * | 6/2004 | Isozaki et al. | 356/237.2 |
| 2008/0059094 | A1 * | 3/2008 | Shimura et al. | 702/81 |
| 2008/0239301 | A1 * | 10/2008 | Yokota et al. | 356/237.2 |
| 2009/0315988 | A1 * | 12/2009 | Fukazawa | 348/126 |
| 2010/0106443 | A1 * | 4/2010 | Shimura et al. | 702/81 |
| 2010/0214560 | A1 * | 8/2010 | Yagyu et al. | 356/237.1 |

FOREIGN PATENT DOCUMENTS

| | | |
|---|---|---|
| EP | 2 159 569 A1 | 3/2010 |
| EP | 2159569 A1 * | 3/2010 |
| JP | 2004132773 | 4/2004 |
| JP | 2004-317126 | 11/2004 |
| JP | 2010014735 | 1/2010 |
| WO | WO 02/061368 A2 | 8/2002 |

OTHER PUBLICATIONS

European Search Report for related European Patent Application No. EP 11166859.6, report dated Aug. 18, 2011.

* cited by examiner

*Primary Examiner* — Christopher S Kelley
*Assistant Examiner* — Ana Picon-Feliciano
(74) *Attorney, Agent, or Firm* — Miller, Matthias & Hull LLP

(57) ABSTRACT

An appearance inspection apparatus has conveying means for conveying an inspection object and surface shape inspecting means for inspecting the surface shape of the inspection object. The surface shape inspection means has a slit beam irradiating section for irradiating a band-shaped slit beam on the surface of the inspection object, an area sensor camera for capturing images of the slit beam, first and second optical mechanisms for receiving reflected lights of the slit beam on the downstream and upstream sides in a conveyance direction, respectively, and guiding them to the area sensor camera, and a shape judging section for judging appropriateness of the surface of the inspection object based on images captured by the area sensor camera. Optical paths of the first and second optical mechanisms allow images of the reflected lights to be formed on the area sensor camera in a state of being aligned laterally.

5 Claims, 10 Drawing Sheets

APPEARANCE INSPECTION APPARATUS

FIELD OF THE DISCLOSURE

The present disclosure relates to an apparatus for inspecting the appearance of a medicine (tablet, capsule etc.), a food product, a machine component, an electronic component or the like (hereinafter, referred to as an "inspection object").

BACKGROUND OF THE DISCLOSURE

Conventionally, as an apparatus for inspecting the appearance of the surface of an inspection object as mentioned above, the apparatus disclosed in the Japanese Unexamined Patent Application Publication No. 2004-317126 is known, for example.

In this apparatus, a laser slit beam is irradiated on the surface of an inspection object, the irradiated laser slit beam is imaged by an appropriate imaging device, and information on the height of the surface of the inspection object is obtained by analyzing the obtained image according to a light-section method. On the basis of the obtained height information, flaws, chips and the like which are present in the surface of the inspection object are detected and further the volume of the inspection object is calculated.

By the way, in inspection of this type which uses a light-section method, there is a problem that, when a laser slit beam is imaged from only one direction, there may occur some blind spots which cannot be seen in the imaging direction depending on the surface shape of the inspection object and accurate inspection cannot be performed for these blind spots because reflected lights of the laser beam cannot be received. As shown in FIG. 18, if a defect 200 is present in the surface of an inspection object K, there occur a blind spot 200a when the inspection object K is imaged by a camera 201 from the direction indicated by the solid line. However, the blind spot 200a can be imaged by imaging the inspection object K from the opposite direction (the direction indicated by the two-dot chain line).

Therefore, the applicant of the present application has suggested, in the Japanese Patent Application Nos. 2009-281084 and 2009-281087, an appearance inspection apparatus in which the laser slit beam is imaged from the front and from the rear in the direction of conveying the inspection object.

This appearance inspection apparatus, as shown in FIG. 19, has, as a image capturing device 110, an area sensor camera 111 disposed above a conveyance path of a straight conveying section 100, a slit beam emitter 112 emitting a band-shaped slit beam, mirrors 113, 114 for guiding the slit beam emitted from the slit beam emitter 112 toward just below the area sensor camera 111 to irradiate the slit beam on an inspection object K being conveyed by the straight conveying section 100, mirrors 115, 116 for receiving a reflected light of the slit beam irradiated on the inspection object K on the downstream side in the conveyance direction of the straight conveying section 100 (the direction of the arrow) and guiding it into the area sensor camera 111, and mirrors 117, 118 for receiving a reflected light of the slit beam on the upstream side in the conveyance direction and guiding it into the area sensor camera 111.

The area sensor camera 111 has an area sensor comprising picture elements arranged in lines and columns, and, as shown in FIG. 20, images of the two reflected lights are formed on the area sensor in a state of being aligned in the direction orthogonal to the raster direction of the area sensor (in a state of being aligned vertically) within the region of the area sensor (the region indicated by the one-dot chain line). It is noted that, in such a conventional apparatus that a slit beam is imaged from the upstream side and from the downstream side in a conveyance direction using two mirrors on each side, images thereof are necessarily formed on the area sensor in the state of being aligned vertically.

For lines within a preset width, for example, line widths A and B shown in FIG. 20, the area sensor camera 111 scans in the raster direction and outputs, for each of the line widths A and B, image data comprising pixels arranged in lines and columns with luminance data, and the output image data are used for inspection.

SUMMARY OF THE DISCLOSURE

By the way, for performing highly accurate inspection in the above-described appearance inspection apparatus, it is necessary to increase the shutter speed of the area sensor camera 111 to obtain images of the slit beam with high density along the direction of conveying the inspection object.

However, the above conventional appearance inspection apparatus has the following problem. In this apparatus, the captured images of the irradiated slit beam have not a line-shaped region but a band-shaped region of a predetermined width because the images are captured in oblique directions, and in particular, images of the reflected lights guided from the two sides, the front and rear sides, are formed on the area sensor camera 111 in the state of being aligned vertically. Because of the above reasons, as shown in FIG. 20, it is necessary to output data in the raster direction for the two line widths A and B, and therefore longer time is required for outputting the image data. Therefore, it is not possible to obtain a high shutter speed which is necessary for performing highly accurate inspection.

The present disclosure has been achieved in view of the above-described circumstances, and an object thereof is to provide a so-called three-dimensional appearance inspection apparatus using a light-section method, wherein the shutter speed of an area sensor camera can be increased and highly accurate inspection can be achieved as a result thereof.

The present disclosure, for solving the above-described problem, relates to an appearance inspection apparatus having conveying means for conveying an inspection object on a predetermined conveying surface and surface shape inspecting means for inspecting the surface shape of the inspection object being conveyed by the conveying means, wherein the surface shape inspecting means comprises:

a slit beam irradiating section disposed in the vicinity of the conveying means for irradiating a band-shaped slit beam on the surface of the inspection object in such a manner that the slit beam is radiated vertically to the conveying surface and the irradiation line of the slit beam is orthogonal to a conveyance direction for conveying the inspection object;

an area sensor camera for capturing images of the slit beam irradiated on the surface of the inspection object;

a first optical mechanism which has an optical path for receiving a reflected light of the slit beam irradiated on the surface of the inspection object on the downstream side in the conveyance direction for conveying the inspection object, and guiding the reflected light to the area sensor camera;

a second optical mechanism which has an optical path for receiving a reflected light of the slit beam on the upstream side in the conveyance direction, and guiding the reflected light to the area sensor camera; and a shape judging section for recognizing shape features of the surface of the inspection object on the basis of two images captured by the area sensor camera, and judging appropriateness of the shape of the surface of the inspection object, and the optical paths of the first and second optical mechanisms are for forming images of the reflected lights on an image forming portion of the area sensor camera in a state where they are aligned laterally.

According to this appearance inspection apparatus, the surface shape of an inspection object being conveyed by the conveying means is inspected by the surface shape inspecting means.

That is, initially, a slit beam is irradiated, by the slit beam irradiating section, on the surface of an inspection object being conveyed. Reflected lights of the irradiated slit beam are guided to the area sensor camera through the optical path of the first optical mechanism which receives the reflected light on the downstream side in the conveyance direction and through the optical path of the second optical mechanism which receives the reflected light on the upstream side in the conveyance direction, respectively, and images of the reflected lights are formed within a preset region on the image forming portion of the area sensor camera in a state of being aligned laterally.

The area sensor camera outputs data on the images formed within the preset region in sequence at predetermined shutter intervals. It is noted that, although the position of the slit beam irradiated on the surface of the inspection object is shifted as the inspection object is moved, the area sensor camera outputs, to the shape judging section, image data of the slit beam at least with respect to the entire surface of the inspection object.

The shape judging section judges appropriateness of the surface shape of the inspection object on the basis of two image data per one inspection object which are received from the area sensor camera. That is, on the basis of the received two image data, the shape judging section first calculates data on the three-dimensional shape of the surface of the inspection object using a light-section method for each of the two image data, combines the calculated two data and recognizes features of the surface shape of the inspection object on the basis of the combined data, and then judges appropriateness of the surface shape of the inspection object, for example, the existence of defects and the quality of engraved marks if any exists, on the basis of the recognized features.

Thus, according to the appearance inspection apparatus of the present disclosure, since the optical paths of the first and second optical mechanisms allow images of the reflected lights guided to the area sensor camera through these optical paths to be formed on the image forming portion of the area sensor camera in a state of being aligned laterally, the two images are formed within a region of a predetermined band width on the image forming portion. Therefore, by outputting data on the band width, the two image data can be output simultaneously.

As described above, according to the present disclosure, since two image data can be output simultaneously and the time of outputting the data is therefore reduced to half compared with the conventional appearance inspection apparatus, the shutter speed of the area sensor camera can be increased, which in turn achieves highly accurate appearance inspection.

It is preferable that the two images captured by the area sensor camera have the same top-bottom orientation, from the perspective that it is then not necessary to perform an operation for top-bottom reversal in the shape judging section and the processing can therefore be performed quickly.

For capturing images having the same top-bottom orientation as described above, it is advantageous that each of the first and second optical mechanisms comprises three mirrors, namely, a first mirror which has a reflective surface disposed along the axial direction of a first axis orthogonal to the conveyance direction and parallel to the conveying surface, and receives a reflected light of the slit beam irradiated on the surface of the inspection object with its reflective surface and reflects it, a second mirror which has a reflective surface disposed along the axial direction of a second axis orthogonal to the conveying surface, and receives the light reflected by the first mirror and reflects it, and a third mirror which has a reflective surface disposed along the conveyance direction, and receives the light reflected by the second mirror and reflects it to guide the reflected light to the area sensor camera.

In this case, it is preferable that the first mirrors of the first and second optical mechanisms are configured to receive reflected lights having the same elevation angle. When thus configured, height information obtained from the images correspond to each other and it is therefore not necessary to perform a correction operation or the like later. As a result, it is possible to perform more quick and more accurate inspection.

Further, it is preferable that each of the first and second optical mechanisms has a first angle adjusting section for rotating the respective first mirror about an axis parallel to the first axis and a second angle adjusting section for rotating the respective second mirror about an axis parallel to the second axis.

Adjustment of the angles of the reflective surfaces of the first and second mirrors enables the positions in the vertical direction of the images of the two reflected lights formed on the area sensor camera in a state of being aligned laterally to correspond to each other. As a result, data processing in the shape judging section can be performed quickly.

As described above, according to the present disclosure, since the time of outputting two image data from the area sensor camera can be reduced to half compared with the conventional appearance inspection apparatus, the shutter speed of the area sensor camera can be increased. As a result, image data with high resolution can be obtained and therefore highly accurate appearance inspection can be achieved.

DETAILED DESCRIPTION

Hereinafter, one specific embodiment of the present disclosure will be described on the basis of the drawings.

Figure 1:
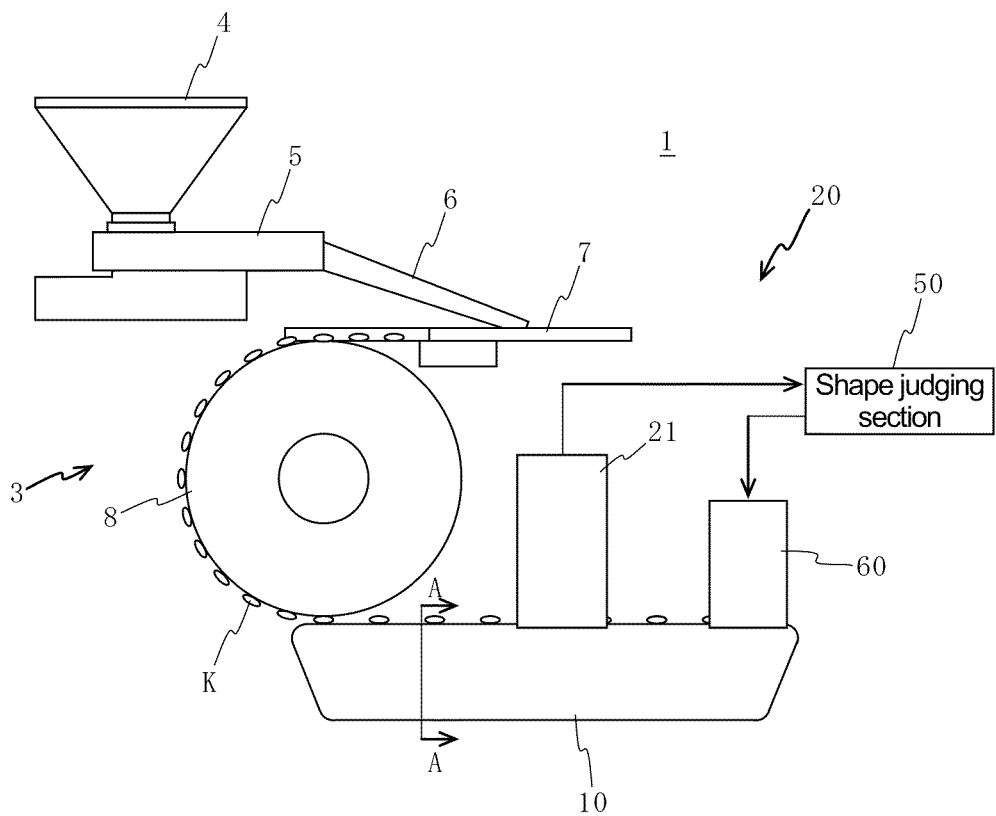
FIG. 1 is a front view of an appearance inspection apparatus according to one embodiment of the present disclosure.

As shown in FIG. 1, an appearance inspection apparatus 1 of the embodiment has a supply section 3 for aligning inspection objects K and supplying them, a straight conveying section 10 for straight conveyance of the supplied inspection objects K, and a surface shape inspecting section 20 for inspecting the surface shape of each of the inspection objects K being conveyed and sorting them.

As examples of the inspection object K in the embodiment, there can be mentioned a medicine (tablet, capsule etc.), a food product, a machine component, an electronic component and the like. However, the inspection object K is not limited thereto.

Hereinafter, each of the above-mentioned sections will be explained in detail.

Supply Section

The supply section 3 comprises a hopper 4 into which a large number of inspection objects K are thrown, a vibrating feeder 5 which moves the inspection objects K discharged from the lower end of the hopper 4 forward by applying vibration to them, a chute 6 on which the inspection objects K discharged from the conveyance end of the vibrating feeder 5 slide down, an aligning table 7 which horizontally rotates and which aligns the inspection objects K supplied from the chute 6 in a line and discharges them, and a rotary conveying section 8 which has a disk-shaped member rotating in a virtual plane and which conveys the inspection objects K discharged from the aligning table 7 in a state where the inspection objects K are sucked and held on the outer peripheral surface of the disk-shaped member. The supply section 3 aligns a large number of inspection objects K in a line and delivers them to the straight conveying section 10 one by one.

Straight Conveying Section

Figure 3:
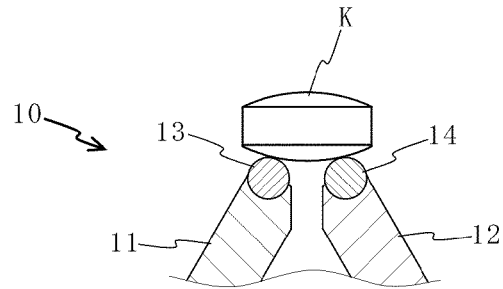
FIG. 3 is a sectional view taken along the arrow line A-A in FIG. 1.

FIG. 3 is a partial sectional view taken along the arrow line A-A in FIG. 1. As shown in FIG. 3, the straight conveying section 10 has side boards 11, 12 arranged to face each other with a predetermined space therebetween, and endless round belts 13, 14 which are guided by guide grooves respectively formed in the upper surfaces of the side boards 11, 12 and which run along the guide grooves.

The space between the side boards 11, 12 is closed by the side boards 11, 12 and other members (not shown) in such a manner that the upper portion of the space is open, and the space is maintained at a negative pressure by means of a not-shown vacuum pump.

Thus, by maintaining the space at a negative pressure, a sucking force due to the negative pressure is produced between the round belts 13, 14 running along the guide grooves. When an inspection object K is loaded on the round belts 13, 14, it is sucked and held on the round belts 13, 14 due to the sucking force, and is conveyed in the running direction of the round belts 13, 14 as the round belts 13, 14 run.

Surface Shape Inspecting Section

The surface shape inspecting section 20 comprises an image capturing section 21, a shape judging section 50 and a sorting section 60.

Figure 4:
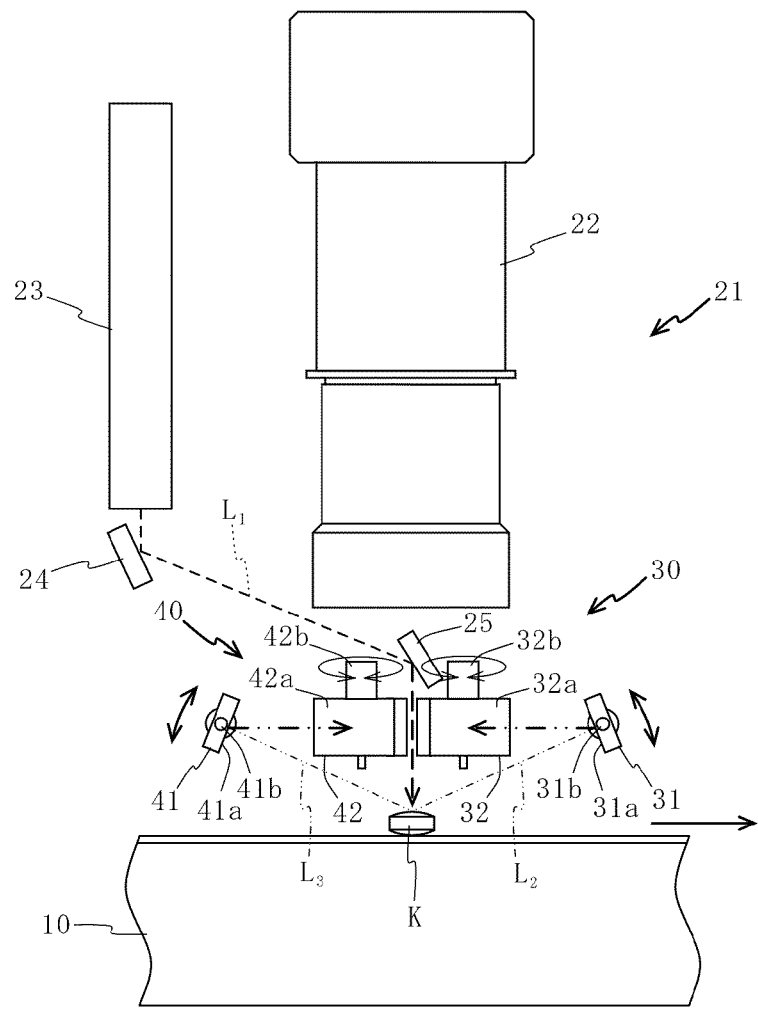
FIG. 4 is a front view of an image capturing section according to the embodiment.

As shown in FIG. 4, the image capturing section 21 has an area sensor camera 22 disposed above a conveyance path of the straight conveying section 10, a slit beam emitter 23 emitting a band-shaped slit beam $L_1$, mirrors 24, 25 for irradiating the slit beam $L_1$ emitted from the slit beam emitter 23 on the conveyance path of the straight conveying section 10, a first optical mechanism 30 for receiving a reflected light $L_2$ of the slit beam $L_1$ on the downstream side in the conveyance direction of the straight conveying section 10 (the direction of the arrow) and guiding it into the area sensor camera 22, and a second optical mechanism 40 for receiving a reflected light $L_3$ of the slit beam $L_1$ on the upstream side in the conveyance direction and guiding it into the area sensor camera 22.

Figure 7:
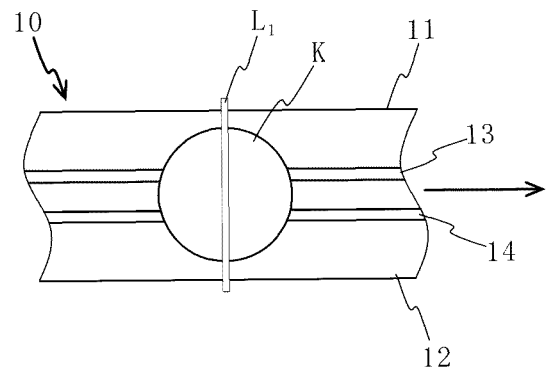
FIG. 7 is an illustration showing a mode of irradiation of a slit beam in the embodiment.

The slit beam emitter 23 and the mirrors 24, 25 allow the slit beam $L_1$ to be radiated vertically downward so that the irradiation line of the slit beam $L_1$ is orthogonal to the conveyance direction in which the inspection object K is conveyed by the straight conveying section 10 (the direction of the arrow). A state where the slit beam $L_1$ is irradiated on the surface of the inspection object K is shown in FIG. 7.

Figure 5:
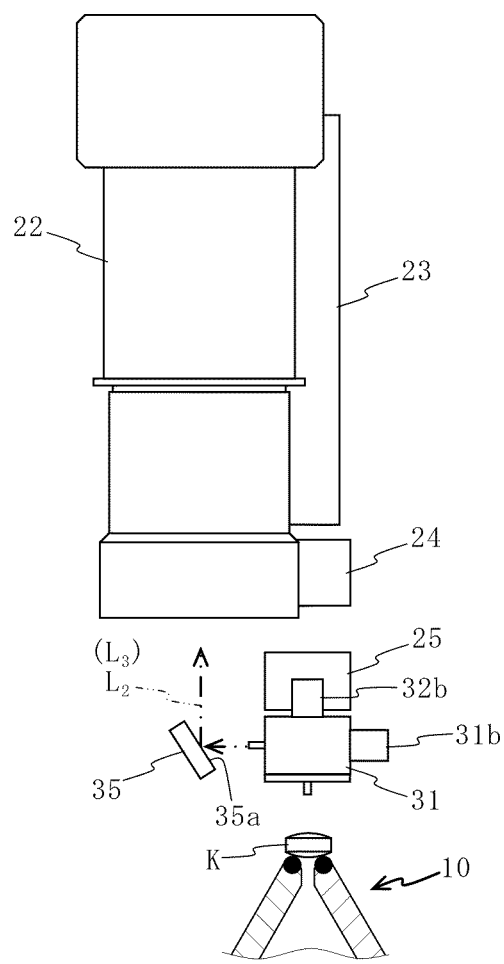
FIG. 5 is a right side view of the image capturing section shown in FIG. 4.
Figure 6:
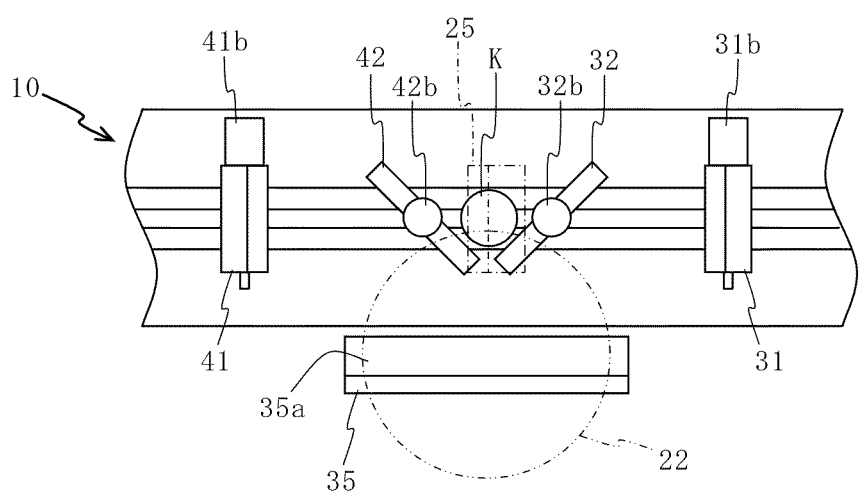
FIG. 6 is a plan view of the image capturing section shown in FIG. 4.

As shown in FIGS. 4 to 6, the first optical mechanism 30 has a first mirror 31 and a second mirror 32, the second optical mechanism 40 has a first mirror 41 and a second mirror 42, and they have a common third mirror 35. It is noted that it is possible to employ a mode in which the third mirror 35 comprises one integrated mirror as shown in the embodiment or a mode in which it comprises two separate mirrors.

The first mirror 31 has a reflective surface 31a disposed along the axial direction of a first axis (virtual axis) orthogonal to the conveyance direction of the straight conveying section 10 and parallel to a conveying surface thereof (conveying surface formed by the round belts 13, 14), and is configured to receive a reflected light $L_2$ of the slit beam $L_1$ irradiated on the surface of the inspection object K with the reflective surface 31a on the downstream side and reflect it.

Similarly, the first mirror 41 has a reflective surface 41a disposed along the axial direction of the virtual first axis, and is configured to receive a reflected light $L_3$ of the slit beam $L_1$ irradiated on the surface of the inspection object K with the reflective surface 41a on the upstream side and reflect it.

The first mirrors 31, 41 has rotary shafts 31b, 41b along the virtual first axis, respectively, and the angles of the reflective surfaces 31a, 41a with respect to a horizontal plane can be adjusted by rotating the rotary shafts 31b, 41b about their respective axes. Each of the rotary shafts 31b, 41b functions as an angle adjusting section.

The second mirror 32 has a reflective surface 32a disposed along the axial direction of a second axis (virtual axis) orthogonal to the conveying surface, and is arranged to receive the light reflected by the first mirror 31 with the reflective surface 32a and reflect it toward the third mirror 35.

Similarly, the second mirror 42 also has a reflective surface 42a disposed along the axial direction of the virtual second axis, and is arranged to receive the light reflected by the first mirror 41 with the reflective surface 42a and reflect it toward the third mirror 35.

The second mirrors 32, 42 have rotary shafts 32b, 42b along the virtual second axis, respectively, and the angles of the reflective surfaces 32a, 42a with respect to a vertical plane can be adjusted by rotating the rotary shafts 32b, 42b about their respective axes. Each of the rotary shafts 32b, 42b functions as an angle adjusting section.

The third mirror 35 has a reflective surface 35a disposed along the conveyance direction, and receives the lights reflected by the second mirrors 32, 42 with the reflective surface 35a in a state where the lights are aligned laterally, and guides the reflected lights being aligned laterally into the area sensor camera 22.

The area sensor camera 22 has an area sensor comprising picture elements arranged in lines and columns. The reflected light $L_2$ received on the downstream side and the reflected light $L_3$ received on the upstream side are guided into the area sensor camera 22 in a state of being aligned laterally, through the optical path of the first optical mechanism 30 and through the optical path of the second optical mechanism 40, respectively, and images thereof are formed on the area sensor in the state of being aligned laterally.

Figure 8A:
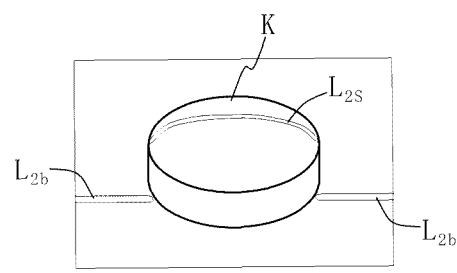
FIG. 8A is an illustration showing when the slit beam shown in FIG. 7 is viewed from the front in a conveyance direction for conveying an inspection object.
Figure 8B:
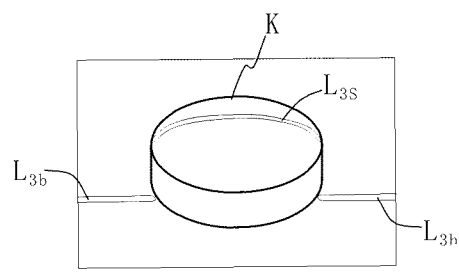
FIG. 8B is an illustration showing when the slit beam shown in FIG. 7 is viewed from the rear in the conveyance direction.

FIGS. 8A and 8B show views of the inspection object K when viewed diagonally from above with naked eyes on the downstream side and on the upstream side, respectively, the slit beam $L_1$ being irradiated on the inspection object K. As shown in the figures, reflected lights $L_{2s}$, $L_{3s}$ reflected from the surface of the inspection object K are shifted upward from reflected lights $L_{2b}$, $L_{3b}$ reflected from the base surface, respectively. This is caused by the fact that the visual direction intersects the irradiation direction of the slit beam $L_1$. This is called a so-called light-section method, and a slit beam irradiated on the surface of an object looks shifted upward from a slit beam irradiated on a base surface depending on the height of the surface of the object. In the area sensor camera 22, such images are formed on the area sensor thereof.

Figure 9:
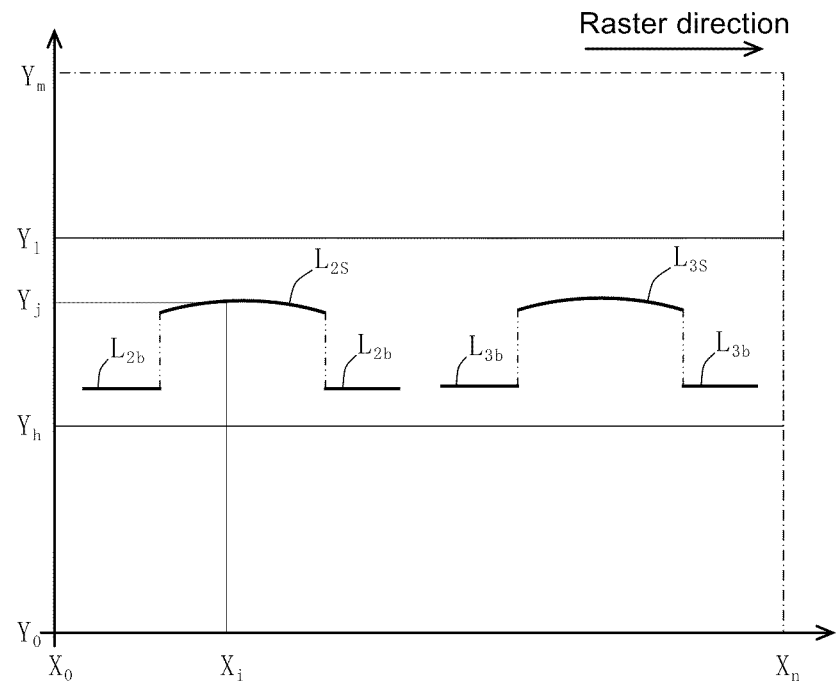
FIG. 9 is an illustration showing an image which is formed on an area sensor camera according to the embodiment.

An example of the image captured by the area sensor camera 22 is shown in FIG. 9. FIG. 9 shows a state where an image of the reflected lights $L_{2s}$, $L_{2b}$ guided through the optical path of the first optical mechanism 30 and an image of the reflected lights $L_{3s}$, $L_{3b}$ guided through the optical path of the second optical mechanism 40 are formed on the area sensor (within the region indicated by the one-dot chain line).

It is noted that the area sensor has picture elements in $X_n$ columns in the raster direction and $Y_m$ lines in the direction vertical to the raster direction. The image of the reflected lights $L_{2s}$, $L_{2b}$ and the image of the reflected lights $L_{3s}$, $L_{3b}$ are formed in a state where they are aligned laterally in the raster direction within the range of lines $Y_h$-$Y_1$. Further, the left-right orientations of the formed images are opposite to each other.

The area sensor camera 22 scans data of the picture elements within the range of lines $Y_h$-$Y_1$ in the raster direction in sequence at predetermined shutter release intervals, and reads out luminance data detected by each picture element, and, as shown in FIG. 9, transmits, to the shape judging section 50, as image data, data in which position data $(X_i, Y_j)$ comprising a pixel position in the X-direction $(X_i)$ and a pixel position $(Y_j)$ which has the maximum luminance in the column is related to the luminance data. In this way, the volume of the transmitted data is smaller compared with when luminance data for all of the picture elements are transmitted, and therefore the speed of transmitting the data and the processing speed of the shape judging section 50 can be increased. As a result, the processing can be performed quickly.

It is noted that the area sensor camera 22 transmits, to the shape judging section 50, the image data at least while the slit beam $L_1$ is irradiated on the surface of the inspection object K as frame images which are obtained at the times of shutter releases.

By the way, as described above, a slit beam irradiated on the surface of an object looks shifted upward from a slit beam irradiated on a base surface depending on the height of the surface of the object. The amount of shift is different depending on the visual angle (elevation angle).

Therefore, the first mirrors 31, 41 are preferably disposed in such a manner that they have the same elevation angle, in such a manner that they are respectively away from the irradiation position of the slit beam $L_1$ on the conveyance path by the same distance in the forward and backward directions and their upper height positions are the same height position.

When thus configured, height information included in the two images, the front and rear images, captured by the area sensor camera 22 correspond to each other, and therefore it is not necessary to perform a correction operation in a later step.

Further, it is preferred, for processing in later steps, that the positions in the column direction of the two images captured by the area sensor camera 22 are the same. For this reason, in the embodiment, the positions of the two images formed on the area sensor camera 22 are adjusted using a measure shown in FIGS. 10 to 12 before starting inspection.

Figure 10:
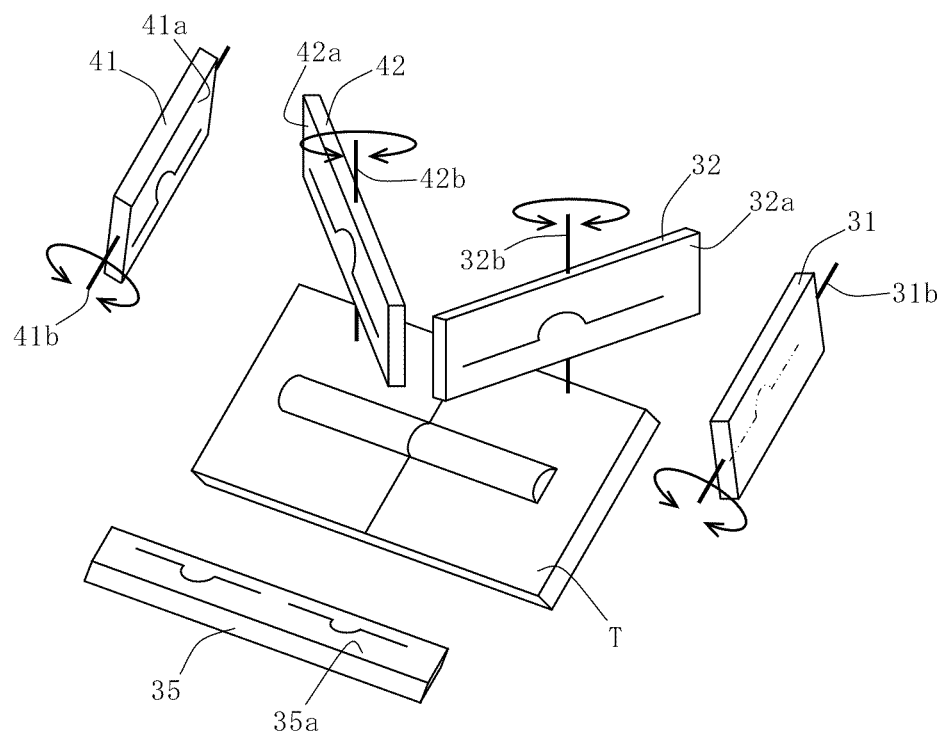
FIG. 10 is an illustration for explaining a mode of adjusting the angles of mirrors of a first optical mechanism and a second optical mechanism according to the embodiment.

That is, as shown in FIG. 10, first, a test piece T which is formed by a plate-shaped substrate having a half-cylindrical protrusion formed thereon is loaded on the conveyance path in such a manner that the longitudinal direction of the protrusion is along the conveyance direction, and then a slit beam is emitted from the slit beam emitter 23.

Figure 12:
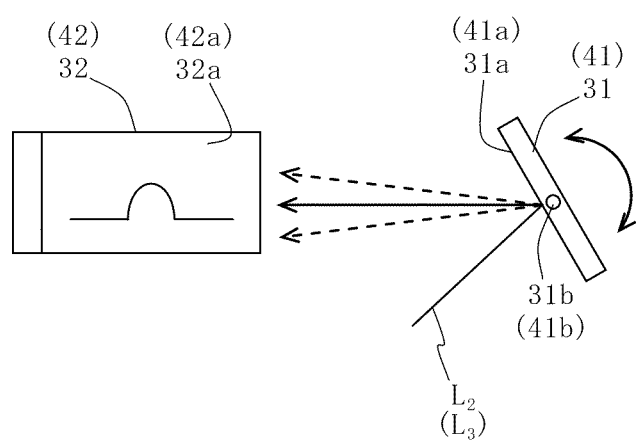
FIG. 12 is an illustration for explaining the mode of adjusting the angles of the mirrors of the first optical mechanism and the second optical mechanism according to the embodiment.
Figure 13:
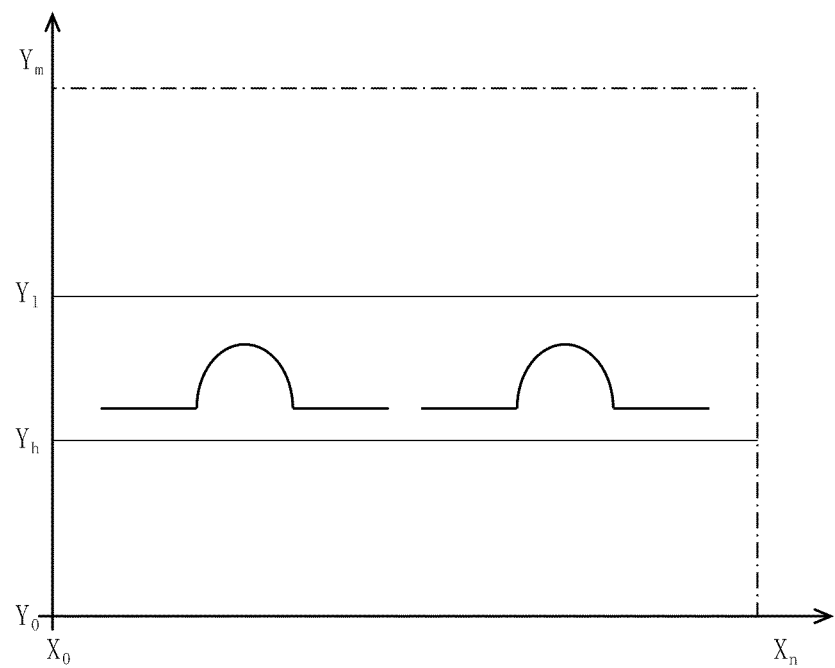
FIG. 13 is an illustration for explaining the mode of adjusting the angles of the mirrors of the first optical mechanism and the second optical mechanism according to the embodiment.

Subsequently, in this state, one or both of the rotary shaft 31b of the first mirror 31 and the rotary shaft 41b of the first mirror 41 are rotated to adjust the angles of the reflective surfaces 31a, 41a with respect to a horizontal plane, as shown in FIG. 12, so that the light-receiving height positions at which the reflected lights $L_2$, $L_3$ are received by the third mirror 35 after being reflected by the second mirrors 32, 42 are the same height position and so that, as shown in FIG. 13, the images of the reflected lights $L_2$, $L_3$ are formed between line $Y_h$ and line $Y_i$ on the area sensor.

Figure 11:
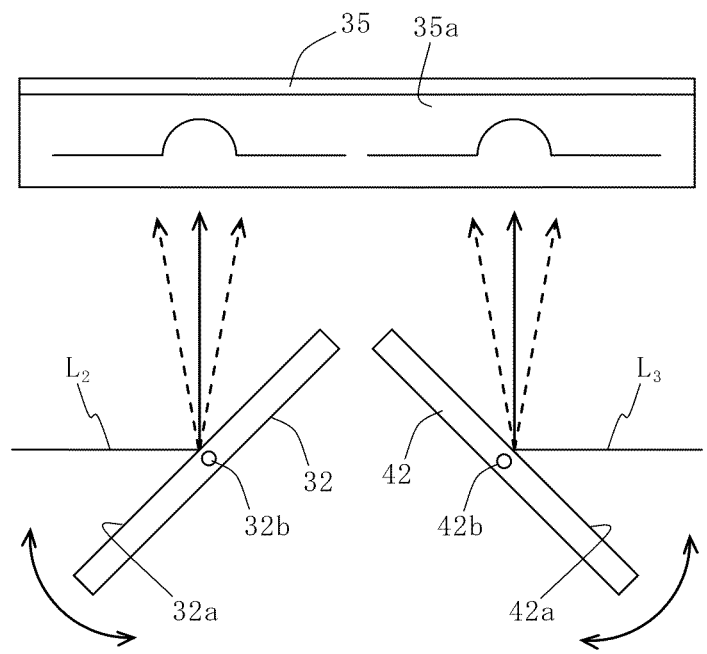
FIG. 11 is an illustration for explaining the mode of adjusting the angles of the mirrors of the first optical mechanism and the second optical mechanism according to the embodiment.

Thereafter, as shown in FIG. 11, one or both of the rotary shaft 32b of the second mirror 32 and the rotary shaft 42b of the second mirror 42 are rotated to adjust the angles of the reflective surfaces 32a, 42a with respect to a vertical plane, and thereby the light-receiving positions in the horizontal direction on the third mirror 35 at which the reflected lights $L_2$, $L_3$ are received are adjusted. In this way, the images of the reflected lights $L_2$, $L_3$ are formed on the area sensor without extending to the outside in the X-direction.

The above-described adjustment allows, as shown in FIG. 13, images of the reflected lights $L_2$, $L_3$ to be formed between line $Y_h$ and line $Y_1$ on the area sensor in such a manner that they do not extend to the outside in the X-direction and their corresponding height positions are on the same line.

Figure 2:
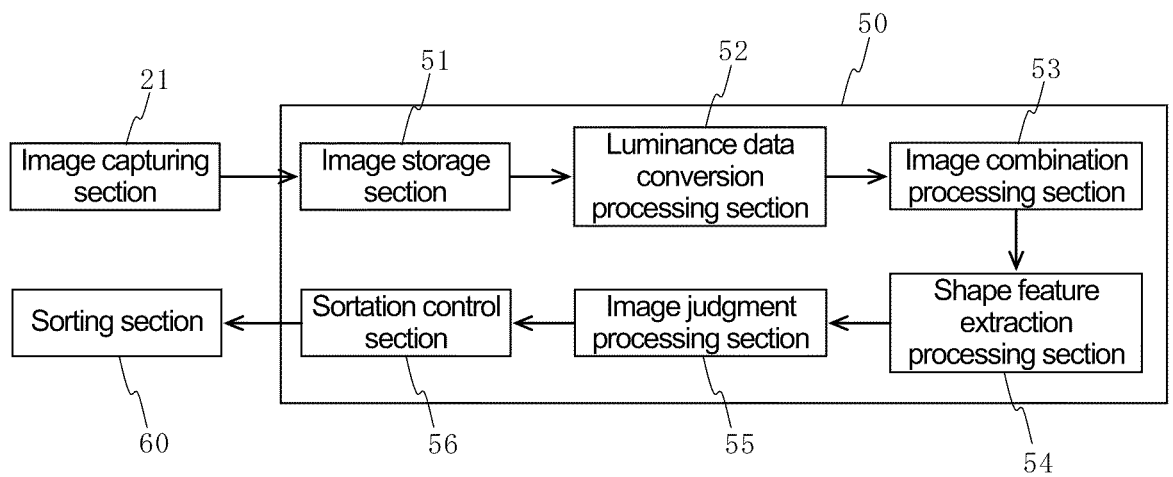
FIG. 2 is a block diagram showing a configuration of a shape judging section according to the embodiment.

The shape judging section 50 comprises, as shown in FIG. 2, an image storage section 51, a luminance data conversion processing section 52, image combination processing section 53, shape feature extraction processing section 54, a shape judgment processing section 55 and a sortation control section 56.

In the image storage section 51, image data (frame images) received from the image capturing section 21 are stored.

The luminance data conversion processing section 52 reads out the frame images stored in the image storage section 51 and converts position data deriving from height components into luminance data by performing the processing described below, the luminance data being set according to the height components. Thereby, new image data in which the height components are represented by luminance data are generated.

Figure 14:
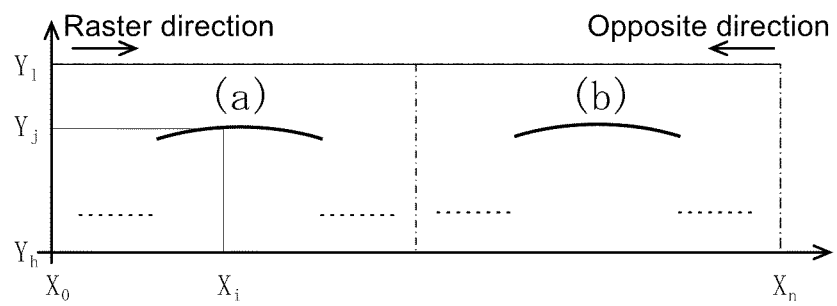
FIG. 14 is an illustration for explaining processing of a luminance data conversion processing section according to the embodiment.
Figure 15:
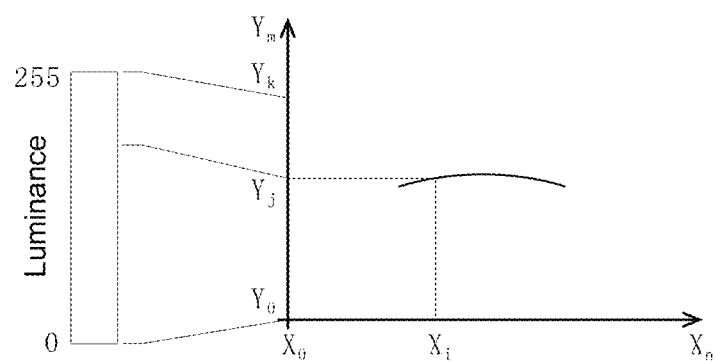
FIG. 15 is an illustration for explaining the processing of the luminance data conversion processing section according to the embodiment.

Specifically, the luminance data conversion processing section 52 first reads out the fame image data in sequence, and, for each of the frame images, as shown in FIG. 14, scans a region (a) in the raster direction and detects pixel positions $(X_i, Y_j)$ at which luminance data is present, and, as shown in FIG. 15, converts the data $(Y_j)$ relating to the pixel position corresponding to the height component into luminance data having 256 gradations, thereby generating image data comprising pixel positions $(X_i)$ and luminance data.

Similarly, with respect to a region (b), the luminance data conversion processing section 52 scans in the direction opposite to the raster direction and performs similar processing, thereby generating image data comprising pixel positions $(X_i)$ and luminance data.

The conversion is performed in sequence for all of the frame images, and thereby new image data (image data which comprises position data in a two-dimensional plane and luminance data representing height information at the positions, and, hereinafter, referred to as "luminance image data") is generated for each of the regions (a), (b).

It is noted that, needless to say, the images of the slit beam $L_1$ which are captured in the two directions exist in the regions (a), (b), respectively, and luminance image data is generated by the above-described processing for each of the images captured in the two directions.

Further, the dotted lines in FIG. 14 represent images of the slit beam irradiated on the base surface and image data thereof are disregarded in the above-described processing because they are not necessary for subsequent processing.

Furthermore, although the left-right orientations of the two images are opposite to each other, scanning the two images in the directions opposite to each other as described above allows the images after the conversion to be corrected images, and thereby it is not necessary to perform a reversal operation in a later step.

The image combination processing section 53 performs processing for generating one luminance image data by combining the luminance image data of the images captured in the two directions which have been generated by the luminance data conversion processing section 52. When the inspection object K is imaged diagonally from above on the downstream side in the conveyance direction, a reflected light from the rear portion of the inspection object K is weak, and when it is imaged diagonally from above on the upstream side in the conveyance direction, a reflected light from the front portion thereof is weak. Therefore, the image data with respect to these portions are inaccurate.

Figure 16:
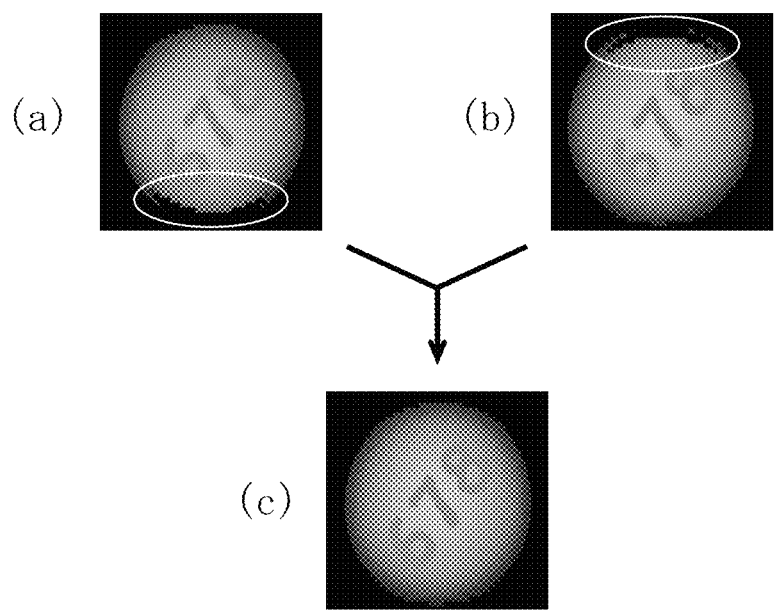
FIG. 16 is an illustration for explaining processing of an image combination processing section according to the embodiment.

An image after an image of an inspection object K which is captured on the downstream side in the conveyance direction is converted by the luminance data conversion processing section 52 is shown in FIG. 16(a), and similarly, an image after an image thereof which is captured on the upstream side in the conveyance direction is converted is shown in FIG. 16(b). In FIG. 16(a), an upper portion of the image (surrounded by the white line) is inaccurate, and in FIG. 16(b), a lower portion of the image (surrounded by the white line) is inaccurate. Accordingly, by combining these two images, for example, when a data is missing in either of them, applying the existent data, and, when a data exists in both of them, applying the average value of them, an image in which the entire surface of the inspection object K is shown accurately as shown in FIG. 16(c) can be obtained.

The shape feature extraction processing section 54 performs processing for extracting shape features on the basis of the combined image generated by the image combination processing section 53. Specifically, the combined image is smoothed by means of a so-called smoothing filter, and feature image data in which the difference between the obtained smoothed image data and the combined image data is evaluated is generated.

Figure 17:
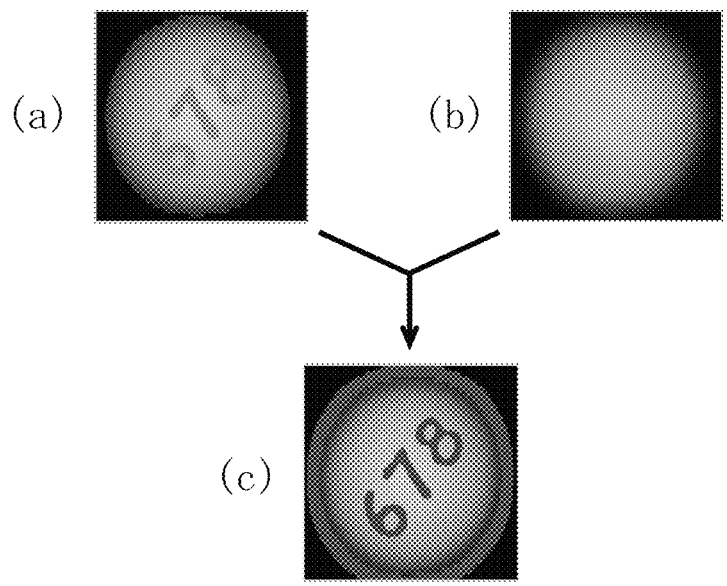
FIG. 17 is an illustration for explaining processing of a shape feature extraction processing section according to the embodiment.
Figure 18:
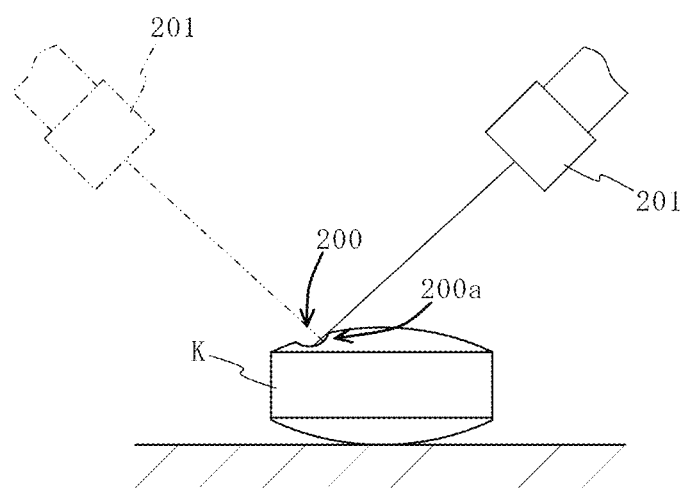
FIG. 18 is an illustration of conventional image capturing.
Figure 19:
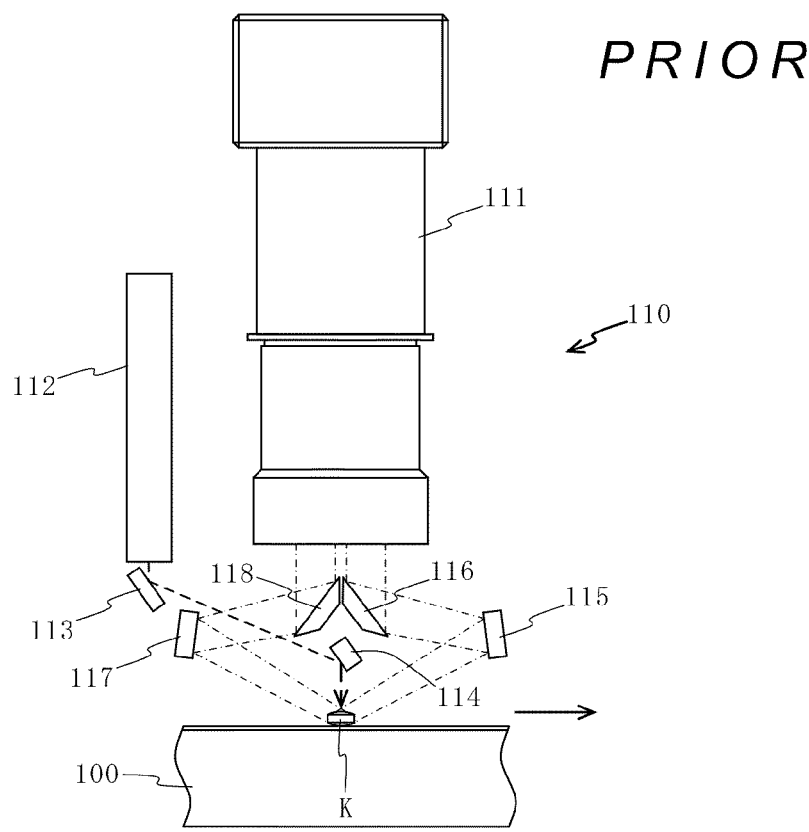
FIG. 19 is a front view of a conventional image capturing device.
Figure 20:
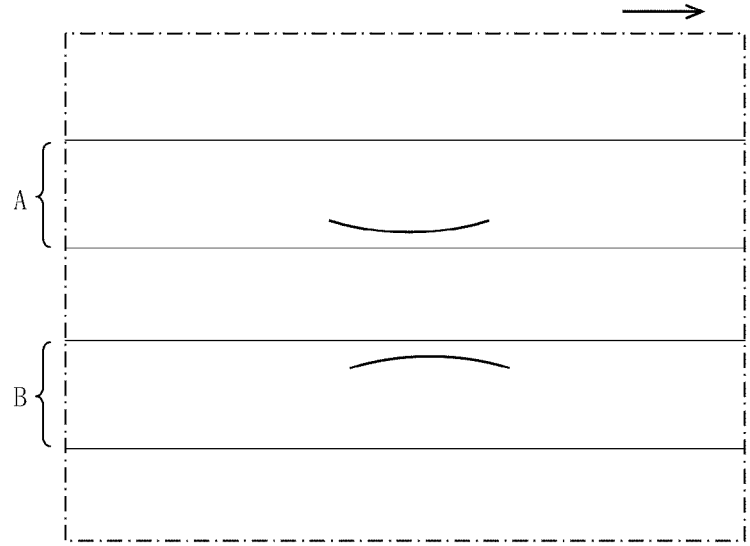
FIG. 20 is an illustration showing images captured by the conventional image capturing device.

The combined image is an image in which the height components have been converted into the luminance data, and the luminance represents the height of the surface of the inspection object K. Therefore, by subtracting the smoothed image from the combined image, an image in which a portion where the amount of variation in the height direction of the surface is emphasized can be obtained. For example, as shown in FIG. 17, by subtracting a smoothed image (FIG. 17(b)) from a combined image (FIG. 17(a)), as shown in FIG. 17(c), the outer contour of the inspection object K and the figure "678" engraved in the surface (A surface) are emphasized as a deep color portion.

On the basis of the feature image relating to the surface shape of the inspection object K which has been generated by the shape feature extraction processing section 54, the shape judgment processing section 55 judges the quality of the surface of the inspection object K, such as appropriateness of engraved marks, the existence of chips etc., by comparing the feature image with data relating to the appropriate surface shape.

The sorting control section 56 receives a result of the judgment from the shape judgment processing section 55. When it receives a judgment result that a inspection object K is defective, it transmits a sorting signal to the sorting section 60 at the timing when the inspection object K judged to be defective reaches the sorting section 60.

The sorting section 60 is provided at the conveyance end of the straight conveying section 10, and has a sorting and collecting mechanism, a good product collecting chamber and a defective product collecting chamber, which are not shown in the figures. When it receives a sorting signal from the sorting control section 56, the sorting and collecting mechanism is activated, and good products among the inspection objects K conveyed to the conveyance end of the straight conveying section 10 are collected into the good product collecting chamber and defective products among them are collected into the defective product collecting chamber.

According to the appearance inspection apparatus 1 of the embodiment having the above-described configuration, initially, while inspection objects K are conveyed by the straight conveying section 10, images of a slit beam $L_1$ irradiated on the surface of each of the inspection objects K are captured by the image capturing section 21 and the captured image data are transmitted from the image capturing section 21 to the shape judging section 50.

Subsequently, on the basis of the captured images, appropriateness of the surface shape is automatically inspected for each of the inspection objects K in the shape judging section 50. According to the inspection results, the inspection objects K are automatically sorted by the sorting section 60 into good products and defective products.

In the appearance inspection apparatus 1 of the embodiment, when the images of the slit beam $L_1$ are captured, images of the reflected lights $L_2$, $L_3$ which are respectively guided through the optical path of the first optical mechanism 30 on the downstream side in the conveyance direction and through the optical path of the second optical mechanism 40 on the upstream side in the conveyance direction are formed on the area sensor of the area sensor camera 22 in a state of being aligned laterally. Therefore, it is possible to read out image data on the two images by scanning a line width for one image in the raster direction, and therefore the time of outputting the data can be reduced to half compared with the conventional apparatus.

Therefore, it is possible to double the shutter speed of the area sensor camera 22 compared with the conventional apparatus, and thereby it is possible to obtain an image with high resolution. Therefore, highly accurate appearance inspection can be achieved.

Since the two images captured by the area sensor camera 22 have the same top-bottom orientation, it is not necessary to perform an operation for top-bottom reversal in the shape judging section 50. Therefore, the processing can be performed quickly.

Further, the first mirrors 31, 41 of the first and second optical mechanisms 30, 40 are configured to respectively receive the reflected lights $L_2$, $L_3$ which have the same elevation angle. Therefore, height information obtained from the images of the reflected lights $L_2$, $L_3$ correspond to each other, and therefore it is not necessary to perform a correction operation or the like later. Therefore, more quick and more accurate inspection can be performed.

Furthermore, since the angles of the reflective surfaces 31a, 41a of the first mirrors 31, 41 and the angles of the reflective surfaces 32a, 42a of the second mirrors 32, 42 can be adjusted, the images of the two reflected lights $L_2$, $L_3$ can be formed on the area sensor camera 22 in a state where the positions in the line direction of the images correspond to each other. Therefore, it is not necessary to perform a correction operation, such as position correction, in the shape judging section 50. Also in this respect, the data processing can be performed quickly.

Thus, although one embodiment of the present disclosure has been described, the present disclosure should not be limited thereto and other embodiments are possible without departing form the spirit of the present disclosure.

What is claimed is:

1. An appearance inspection apparatus having conveying means for conveying an inspection object on a predetermined conveying surface in a conveyance direction for conveying the inspection object and surface shape inspecting means for inspecting the surface shape of the inspection object being conveyed by the conveying means, wherein the surface shape inspecting means comprises:

a slit beam irradiating section disposed in the vicinity of the conveying means for irradiating a band-shaped slit beam on the surface of the inspection object in such a manner that the slit beam is radiated vertically to the conveying surface and the irradiation line of the slit beam is orthogonal to the conveyance direction;

an area sensor camera for capturing images of the slit beam irradiated on the surface of the inspection object;

a first optical mechanism which has an optical path for receiving a reflected light of the slit beam irradiated on a portion of the surface of the inspection object on the downstream side in the conveyance direction, and guiding the reflected light to the area sensor camera;

a second optical mechanism which has an optical path for receiving a reflected light of the slit beam on the same portion of the surface of the inspection object on the upstream side in the conveyance direction and guiding the reflected light to the area sensor camera; and a shape judging section for recognizing shape features of the surface of the inspection object on the basis of the images captured by the area sensor camera and judging appropriateness of the shape of the surface of the inspection object, wherein:

each of the first and second optical mechanisms has a first mirror which has a reflective surface disposed along the axial direction of a first axis orthogonal to the conveyance direction and parallel to the conveying surface, and receives a reflected light of the slit beam irradiated on the surface of the inspection object with the reflective surface and reflects it, a second mirror which has a reflective surface disposed along the axial direction of a second axis orthogonal to the conveying surface, and receives the light reflected by the first mirror and reflects it, a third mirror which has a reflective surface disposed along the conveyance direction, and receives the light reflected by the second mirror and reflects it to guide the reflected light to the area sensor camera, a first angle adjusting section for rotating the respective first mirror about an axis parallel to the first axis, and a second angle adjusting section for rotating the respective second mirror about an axis parallel to the second axis;

the optical paths of the first and second optical mechanisms are for forming images of the reflected lights within a band region in an image forming portion region of the area sensor camera in a state where they are aligned laterally, the band region having a width smaller than that of the image forming portion region in a column direction orthogonal to a line direction which is a raster direction; and the area sensor camera is configured to scan data of each of the images formed within the band region and output the data to the shape judging section.

2. The appearance inspection apparatus according to claim 1, wherein the first mirrors of the first and second optical mechanisms are configured to receive reflected lights having the same elevation angle.

3. The appearance inspection apparatus according to claim 1, wherein the optical paths of the first and second optical mechanisms are configured so that the laterally aligned images are positioned at the same position in the column direction.

4. The appearance inspection apparatus according to claim 1, wherein the area sensor camera is configured to scan data of each of the images formed in the band region in the line direction and output, to the shape judging section, position data including a first pixel position $(X_i)$ in the line direction and a second pixel position $(Y_j)$ in the column direction, the second pixel position $(Y_j)$ having a maximum luminance in the column of the first pixel position $(X_i)$.

5. The appearance inspection apparatus according to claim 4, wherein
the shape judging section is configured to:
generate luminance image data containing luminance data converted from a value of the second pixel position ($Y_j$) for each of the images on the basis of the data of the images input from the area sensor camera;
combine the generated luminance image data; and
recognize shape features of the surface of the inspection object on the basis of the combined luminance image data and judge appropriateness of the shape of the surface of the inspection object.

\* \* \* \* \*